United States Patent [19]

Satoh et al.

[11] Patent Number: 5,143,648
[45] Date of Patent: Sep. 1, 1992

[54] ASCORBIC ACID DERIVATIVE AND USE AS ANTIOXIDANT

[75] Inventors: Toshio Satoh; Yasunori Niiro; Hisao Kakegawa; Hitoshi Matsumoto, all of Tokushima, Japan

[73] Assignee: Nippon Hypox Laboratories Incorporated, Tokyo, Japan

[21] Appl. No.: 748,176

[22] Filed: Aug. 20, 1991

Related U.S. Application Data

[62] Division of Ser. No. 382,270, Jul. 20, 1989, Pat. No. 5,061,812.

[51] Int. Cl.$^5$ .................... C09K 15/22; C07D 411/12
[52] U.S. Cl. .................................. 252/403; 546/283; 544/215; 544/333
[58] Field of Search ................ 546/283; 544/215, 333; 252/403

[56] References Cited

PUBLICATIONS

Parish et al. Chem. Abstracts, vol. 96; 200072u (1982).
Chem. Abstracts, vol. 98; 107680x (1983).

*Primary Examiner*—Johann Richter
*Attorney, Agent, or Firm*—Nixon & Vanderhye

[57] ABSTRACT

This invention relates to a novel ascorbic acid derivative having excellent antioxidant action and a process for preparing the same.

Furthermore, this invention also relates to a novel antioxidant comprising the aforementioned ascorbic acid derivative or other known ascorbic acid derivatives.

18 Claims, No Drawings

ASCORBIC ACID DERIVATIVE AND USE AS ANTIOXIDANT

This is a division of application Ser. No. 07/382,270, filed Jul. 20, 1989, U.S. Pat. No. 5,061,812.

BACKGROUND OF THE INVENTION (1) Field of the Invention

This invention relates to an ascorbic acid derivative, a process for preparing the same and an antioxidant comprising an ascorbic acid derivative.

(2) Prior Art

Ascorbic acid has antioxidant action and is used for the purpose of preventing browing of foods, retaining flavor or freshness of foods or the like.

Ascorbic acid, however, is susceptible to decomposition and sometimes hard to produce the above-mentioned effects over a long period.

SUMMARY OF THE INVENTION

It is, therefore, a first object of this invention to provide a novel ascorbic acid derivative eliminating the aforementioned disadvantages of the ascorbic acid. It is a second object of this invention to provide a process for preparing the aforesaid novel ascorbic acid derivative. It is further a third object of this invention to provide an antioxidant comprising an ascorbic acid derivative.

The first object of this invention has been achieved by an ascorbic acid derivative represented by the general formula (Ia):

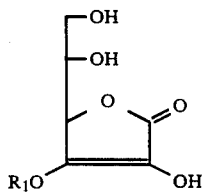

wherein $R_1$ is a group selected from the group consisting of a heterocyclic ring-containing alkyl group, an alkylcarbonylalkyl group, an arylcarbonylalkyl group and an alkoxycarbonylalkyl group containing the terminal alkoxy group having at least 7 carbon atoms.

The second object of this invention has been accomplished by a process for preparing an ascorbic acid derivative represented by the general formula (Ia):

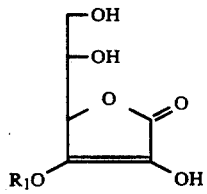

wherein $R_1$ is a group selected from the group consisting of a heterocyclic ring-containing alkyl group, an alkylcarbonylalkyl group, an arylcarbonylalkyl group and an alkoxycarbonylalkyl group containing the terminal alkoxy group having at least 7 carbon atoms, comprising treating a compound represented by the general formula (II):

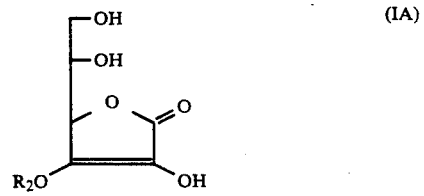

wherein $R_1$ has the same significance as above, with an acid to cleave the dioxolane ring in said compound and form a vic-glycol group.

Furthermore, the third object of this invention has been achieved by an antioxidant comprising an ascorbic acid derivative represented by the general formula (IA):

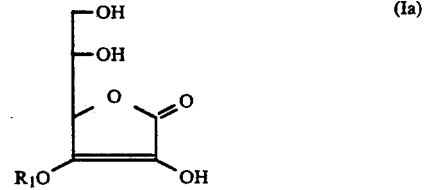

wherein $R_2$ is a group selected from the group consisting of a heterocyclic ring-containing alkyl group, an alkylcarbonylalkyl group, an arylcarbonylalkyl group, an alkoxycarbonylalkyl group, an alkyl group, an aralkyl group and a hydroxycarbonylalkyl group.

The group $R_1$ in the general formula (Ia) representing the novel ascorbic acid derivative of this invention is different in the number of substituent groups defined therein from the group $R_2$ in the general formula (IA) representing the ascorbic acid derivative constituting the antioxidant of this invention. Although the group $R_1$ has four substituent groups, $R_2$ has the total seven substituent groups including the four. The alkoxycarbonylalkyl groups in the group $R_1$ in the general formula (Ia) are restricted to those containing the terminal alkoxy group having at least 7 carbon atoms, whereas such restriction is not placed on the alkoxycarbonylalkyl groups in the group $R_2$ in the general formula (IA). This means that ascorbic acid derivatives excluded from the general formula (Ia) defining the novel ascorbic acid derivative can also be used as the antioxidant of this invention.

The novel ascorbic acid derivative of this invention is initially explained hereinafter.

The novel ascorbic acid derivative of this invention is represented by the general formula (Ia):

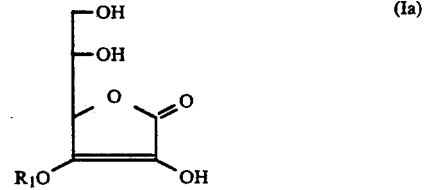

wherein $R_1$ is a group selected from the group consisting of a heterocyclic ring-containing alkyl group, an alkylcarbonylalkyl group, an arylcarbonylalkyl group and an alkoxycarbonylalkyl group containing the terminal alkoxy group having at least 7 carbon atoms.

Heterocyclic ring containing alkyl groups having 1 to 3 nitrogen atoms in the ring are herein preferred as the heterocyclic ring-containing alkyl groups, and examples thereof include groups represented by the general formulae:

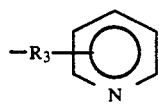

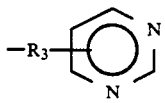

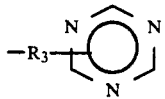

wherein $R_3$ is an alkylene group which may optionally have a branched chain. Particularly preferred heterocyclic ring-containing alkyl groups are pyridylmethyl group, pyrimidylmethyl group, triazylmethyl group and the like.

Examples of the alkylcarbonylalkyl groups include groups represented by the general formula.

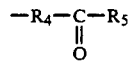

wherein $R_4$ is an alkylene group which may optionally have a branched chain; $R_5$ is an alkyl group which may optionally have a branched chain. Particularly preferred alkylcarbonylalkyl groups are

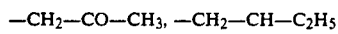

$-CH_2-CO-CH_3, -CH_2-CH-C_2H_5$ and the like.

Furthermore, examples of the arylcarbonylalkyl groups include groups represented by the general formula:

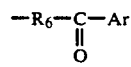

wherein $R_6$ is an alkylene group which may optionally have a branched chain; Ar is an aryl group which may optionally have a substituent group on the ring. Particularly preferred arylcarbonylalkyl groups are $-CH_2-CO-C_6H_5$ and the like.

Examples of the alkoxycarbonylalkyl groups containing the terminal alkoxy group having at least 7 carbon atoms include groups represented by the general formula:

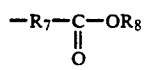

wherein $R_7$ is an alkylene group which may optionally have a branched chain; $R_8$ is an alkyl group of 7 or more carbon atoms which may optionally have a branched chain. Particularly preferred alkoxycarbonylalkyl groups are $-CH_2-CO-O-n-C_{10}H_{21}$ and the like.

The novel ascorbic acid derivative of this invention has excellent antioxidant action and can be preferably used as food antioxidants or beautifying and whitening cosmetics.

The process for preparing the novel ascorbic acid derivative represented by the above-mentioned general formula (Ia) of this invention is explained hereinafter.

In the process of this invention, a compound represented by the general formula (II):

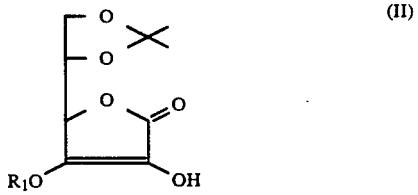

wherein $R_1$ is a group selected from the group consisting of a heterocyclic ring-containing alkyl group, an alkylcarbonylalkyl group, an arylcarbonylalkyl group and an alkoxycarbonylalkyl group containing the terminal alkoxy group having at least 7 carbon atoms, is used as a starting material.

Such a compound represented by the formula (II) is obtained by ketalizing ascorbic acid according to a conventional method to provide 5,6-O-isopropylideneascorbic acid represented by the formula (III):

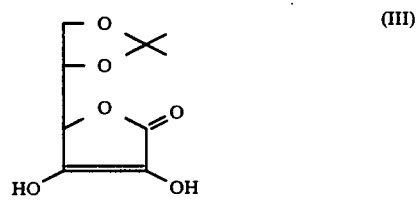

and further reacting the resulting compound (III) with an organic halide represented by the general formula: $R_1X$ wherein $R_1$ is the same as the group $R_1$ in the general formula (II); X is a halogen atom, to etherify the hydroxyl group at the 3-position of the compound (III). This dehydrohalogenation may be carried out either according to the Williamson reaction or in an organic phase-aqueous phase system using a phase transfer catalyst.

According to the process of this invention, the compound (II) as a starting material is treated with an acid to cleave the dioxolane ring in the above-mentioned compound to form a vic-glycol group. Thereby the desired ascorbic acid derivative represented by the general formula (Ia) is obtained.

Example of the acid used for the reaction include hydrochloric acid, acetic acid, sulfuric acid, p-toluenesulfonic acid, methanesulfonic acid, camphorsulfonic acid and the like. The reaction is preferably carried out in at least one organic solvents selected from methanol, ethanol, dioxane, tetrahydrofuran and 1,2-dimethoxyethane.

The antioxidant of this invention is explained hereinafter.

As explained above, the antioxidant of this invention comprises the ascorbic acid derivative represented by the general formula (IA):

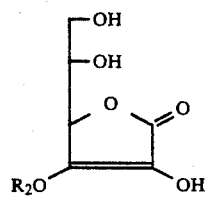

The group $R_2$ in the formula is within a wider scope than the group $R_1$ in the general formula (Ia) representing the novel ascorbic acid derivative as described above, and therefore the ascorbic acid derivative represented by the general formula (IA) includes also known compounds.

Thus, the group $R_2$ includes four substituent groups (heterocyclic ring-containing alkyl group, alkylcarbonylalkyl group, arylcarbonylalkyl group and alkoxycarbonylalkyl group) similar to the group $R_1$, besides those, further three substituent groups of alkyl group, aralkyl group and hydroxycarbonylalkyl group. The term "alkyl" in the aforesaid substituent groups means a straight or branched alkyl group. The alkoxycarbonylalkyl groups in the group $R_1$ in the general formula (Ia) are restricted to those containing the terminal alkoxy group having at least 7 carbon atoms; however, the group $R_2$ in the general formula (IA) includes a wide scope of alkoxycarbonylalkyl groups without such restriction thereon.

Such an ascorbic acid derivative represented by the general formula (IA) has the ability to eliminate radicals and is preferably used as an antioxidant with advantages in better stability than that of ascorbic acid and conventional ascorbic acid derivatives.

EXAMPLES

Examples of this invention are explained hereinafter.

PREPARATION EXAMPLE 1 [PREPARATION OF NOVEL ASCORBIC ACID DERIVATIVE (IA)]

(1) Synthesis of L-5,6-O-isopropylideneascorbic acid

Ascorbic acid in an amount of 180 g was stirred in 750 ml of acetone and warmed to 40° C. Acetyl chloride in a volume of 20 ml was added, and stirring was continued to form a slurry layer.

After 3 hours, the slurry layer was cooled with ice to collect deposited precipitates by filtration. The resulting precipitates were washed with a mixture of cold acetone-n-hexane (3:7) on a funnel and dried with silica gel under reduced pressure.

Recrystallization from acetone was then carried out to provide 190 g of L-5,6-O-isopropylidene ascorbic acid (melting point: 206°–208° C.).

(2) Synthesis of L-5,6-O-isopropylidene-3-O-benzoylmethylascorbic acid

In 30 ml of DMSO, was dissolved 4.32 g of the compound obtained in (1). After NaHCO3 in an amount of 1.78 g was added, the resulting solution was stirred at room temperature for 30 minutes. To the solution, was added 4.37 g of phenacyl bromide, and the obtained solution was warmed to 40° C. and stirred for 18 hours. After cooling, 80 ml of $H_2O$ was added, and pH was adjusted to 5 with 4 N hydrochloric acid. The pH-adjusted solution was shaken with ethyl acetate (100 ml×2). Organic layers were combined, washed with water and saturated aqueous sodium chloride, dried over sodium sulfate and concentrated under reduced pressure. The resulting oily substance was subjected to silica gel column chromatography and eluted with a mixture of benzene-ethyl acetate to provide a L-5,6-O-isopropylidene-3-O-benzoylmethylascorbic acid.

(3) Synthesis of L-3-O-benzoylmethylascorbic acid

In 40 ml of a mixture of tetrahydrofuranmethanol (3:1), was dissolved 3.3 g of the compound obtained in (2), and 10 ml of 2 N hydrochloric acid was added to stir the resulting solution at room temperature for 20 hours. The reaction solution was concentrated under reduced pressure, and the residue was recrystallized from ethyl acetate-petroleum ether to afford L-3-O-benzoylmethylascorbic acid (corresponding to compound No. 112 in Table-1).

The resulting compound No. 112 of this invention was used for antioxidant tests described below.

PREPARATION EXAMPLE 2

[Preparation of Novel Ascorbic Acid Derivative]

Procedures were followed in the same manner as in Preparation example 1 to provide novel compound Nos. 110 and 115 shown in Table-1 mentioned below.

Such compounds were used for the antioxidant tests described below.

PREPARATION EXAMPLE 3

[Preparation of Novel Ascorbic Acid Derivative]

(1) Synthesis of L-5,6-isopropylidene-3-O-(3-picoyl) ascorbic acid

In 40 ml of distilled water, was dissolved 1.66 g of NaHCO3, and 80 ml of methyl ethyl ketone was added. To the resulting solution, was added 4.32 g of the L-5,6-O-isopropylideneascorbic acid obtained in (1) of Preparation example 1. The obtained mixture was stirred, and 3.26 g of 3-picoyl chloride, 1.66 g of NaHCO3 and 1.60 g of tetrabutylammonium bromide were added thereto. The resulting mixture was heated to 70° C. and vigorously stirred for 10 hours. The organic layer was separated, and the aqueous layer was adjusted to pH 4 with 4 N hydrochloric acid and shaken with 100 ml of ethyl acetate. Organic layers were combined, washed with water, dried over sodium sulfate and concentrated under reduced pressure. The resulting residue was subjected to silica gel column chromatography and eluted with a mixture of benzene-ethyl acetate to provide L-5,6-isopropylidene-3-O-(3-picoyl)ascorbic acid.

(2) Synthesis of L-3-O-(3-Picoyl) Ascorbic Acid

Operations were performed in the same manner as in (3) of Preparation example 1, except that the compound obtained in (1) was used. Recrystallization from benzene-petroleum ether was carried out to provide L-3-O-(3-picoyl)ascorbic acid (corresponding to compound No. 113 in Table-1).

The obtained compound No. 113 of this invention was used for the antioxidant tests mentioned below.

PREPARATION REFERENTIAL EXAMPLE 1

[Preparation of Other Ascorbic Acid Derivatives]

Procedures were followed in the same manner as in Preparation example 1 to provide compound Nos. 101, 102, 103, 104, 105, 106, 107, 108, 109, 111 and 114 indicated in Table-1 mentioned below.

The resulting compounds were also used for the antioxidant tests described below.

TABLE 1

| Compound No. | $R_1$ | mp | NMR δ value |
|---|---|---|---|
| 101 | $-(CH_2)_{17}CH_3$ | 103° C. | 0.85(3H, m)1.24(32H, m)3.45(3H, m) 4.36(2H, t)4.73(H, s) |
| 102 | $-(CH_2)_{11}CH_3$ | 86–88° C. | 0.85(3H, m)1.25(20H, m)3.35(3H, m) 4.36(2H, t)4.73(H, s) |
| 103 | $-(CH_2)_7CH_3$ | 58–61° C. | 0.86(3H, m)1.27(12H, m)3.50(3H, m) 4.36(2H, t)4.73(H, s) |
| 104 | $-(CH_2)_3CH_3$ | Oily substance | 0.94(3H, m)1.60(4H, m)3.71(3H, m) 4.48(2H, t)4.79(H, d, 1Hz) |
| 105 | $-(CH_2)_4COOC_2H_5$ | Oily substance | 1.21(3H, t)1.76(4H, m)2.36(2H, m) 3.70(3H, m)4.09(2H, q)4.49(2H, t) 4.79(H, s) |
| 106 | $-(CH_2)_3COOC_2H_5$ | Oily substance | 1.21(3H, t)2.17(2H, m)2.47(2H, t) 3.70(3H, m)4.09(2H, q)4.51(2H, t) 4.80(H, s) |
| 107 | $-(CH_2)_3COOH$ | Oily substance | 2.05(2H, m)2.48(2H, t)3.70(3H, m) 4.54(2H, t)4.80(H, s) |
| 108 | $\begin{array}{c}CH_3\\|\\-CH_2-COOC_2H_5\end{array}$ | 141° C. | 1.20(3H, t)1.48(2H, d)3.34(3H, m) 4.15(2H, q)4.81(H, s)5.31(H, q) |
| 109 | $-CH_2COO\text{-}n\text{-}C_4H_9$ | 81° C. | 0.91(3H, t)1.56(4H, m)3.73(3H, m) 4.14(2H, t)4.90(H, d, 2Hz)5.08(2H, s) |
| 110 | $-CH_2COO\text{-}n\text{-}C_{10}H_{21}$ | Oily substance | 0.88(3H, m)1.25(16H, m)3.70(3H, m) 4.28(2H, t)4.90(H, s)5.09(2H, s) |
| 111 | $-CH_2COOC_2H_5$ | Oily substance | 1.29(3H, t)3.68(3H, m)4.27(2H, q) 4.87(H, d, 2Hz)5.03(2H, s) |
| 112 | 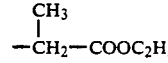 | 92° C. | 3.44(3H, m)4.92(H, s)5.79(H, d, 7Hz) 7.61(3H, m)7.96(2H, m) |
| 113 | 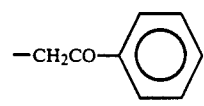 | 154–160° C. | 3.69(3H, m)4.85(H, d, 2Hz)5.61(2H, s) 7.50(H, m)8.0(H, m)8.59(2H, m) |
| 114 | $-(CH_2)_{10}COOH$ | 90° C. | 1.32(16H, m)2.29(2H, t)3.61(3H, m) 4.48(2H, t)4.78(H, s) |
| 115 | $-CH_2COCH_3$ | 143° C. | 2.10(3H, s)3.48(3H, m)4.84(H, s)5.01 (2H, m) |

TEST EXAMPLE 1 (ANTIOXIDANT ACTION EXAMINED BY USING STABLE RADICALS)

Reduction activity of a,α-diphenyl-β-picrylhydrazyl (DPPH) which was a stable free radical was examined according to the M. S. Blois method (Nature, vol. 181, page 1199, 1958) and used as an index to antioxidant action. Thus, specimens were added to 3 ml of a 0.1 mM DPPH solution in ethanol, and absorbance at a wavelength of 517 nm was measured using a spectrophotometer after 20 minutes. The difference in absorbance from the solvent control [0.5% or less of dimethylformamide (DMF)] was taken as the reduction activity.

The 50% radical eliminating concentrations for the test compounds are shown in Table-2.

As can be seen from Table-2, the test compounds were found to have improved antioxidant action. It has been also clarified that the other compound Nos. 102 to 115 have better antioxidant ability than the compound No. 101 wherein $R_1$ is a long-chain alkyl group.

TABLE 2

| Compound No. | 50% radical eliminating concentration |
|---|---|
| 101 | $3.2 \times 10^{-5}$M |
| 102 | 1.8 |
| 103 | 1.9 |
| 104 | 2.3 |
| 105 | 2.0 |
| 106 | 2.1 |
| 107 | 2.7 |
| 108 | 1.9 |
| 109 | 1.8 |
| 110 | 2.3 |
| 111 | 2.2 |
| 112 | 2.3 |
| 113 | 2.3 |
| 114 | 2.4 |
| 115 | 2.2 |

As detailed above, this invention provides a novel ascorbic acid derivative having excellent antioxidant action and a process for preparing the same.

Furthermore, this invention also provides a novel antioxidant comprising the aforementioned ascorbic acid derivative or other known ascorbic acid derivatives.

We claim:

1. An ascorbic acid derivative represented by the formula (Ia):

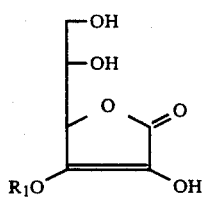

wherein $R_1$ is selected from the group consisting of a heterocyclic ring-containing an alkyl group.

2. An ascorbic acid derivative of claim 1, wherein said heterocyclic ring-containing alkyl group is a heterocyclic ring-containing alkyl group containing 1 to 3 nitrogen atoms in the heterocyclic ring.

3. An ascorbic acid derivative of claim 2, wherein said heterocyclic ring-containing alkyl group is represented by general formula:

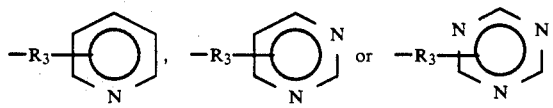

wherein $R_3$ represents an alkylene group which may optionally have a branched chain.

4. An ascorbic acid derivative of claim 3, wherein said heterocyclic ring-containing alkyl group is selected from the group consisting of pyridylmethyl, pyrimidylmethyl and triazylmethyl.

5. An antioxidant composition comprising together with a suitable carrier or diluent an ascorbic acid derivative represented by the formula (IA):

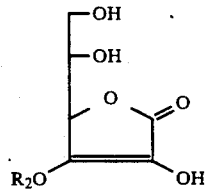

wherein $R_2$ is a group selected from the group consisting of a heterocyclic ring-containing alkyl group, an alkyl-carbonylalkyl group, an arylcarbonylalkyl group, an alkoxycarbonylalkyl group, an alkyl group, an aralkyl group and a hydroxycarbonylalkyl group.

6. An antioxidant of claim 5, wherein said heterocyclic ring-containing alkyl group is a heterocyclic ring-containing alkyl group containing 1 to 3 nitrogen atoms in the heterocyclic ring.

7. An antioxidant of claim 6, wherein said heterocyclic ring-containing alkyl group is represented by the formula:

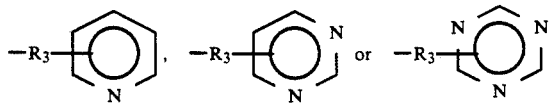

wherein $R_3$ represents an alkylene group which may optionally have a branched chain.

8. An antioxidant of claim 7, wherein said heterocyclic ring-containing alkyl group is selected from the group consisting of pyridylmethyl, pyrimidylmethyl and triazylmethyl.

9. An antioxidant of claim 5, wherein said alkylcarbonylalkyl group is represented by general formula:

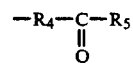

wherein $R_4$ represents an alkylene group which may optionally have a branched chain and $R_5$ represents an alkyl group which may optionally have a branched chain.

10. An antioxidant of claim 9, wherein said alkylcarbonylalkyl group is selected from the group consisting of $-CH_2-CO-CH_3$ and $-CO_2-CO-C_2H_5$.

11. An antioxidant of claim 5, wherein said arylcarbonylalkyl group is represented by general formula:

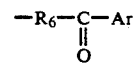

wherein $R_6$ represents an alkylene group which may optionally have a branched chain and Ar is an aryl group which may optionally have a substituent thereon.

12. An antioxidant of claim 11, wherein said arylcarbonylalkyl group is $-CH_2-C_6H_5$.

13. An antioxidant of claim 5, wherein said arylcarbonylalkyl group is represented by the formula:

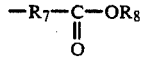

wherein $R_7$ represents an alkylene group which may optionally have a branched chain and $R_8$ is an alkyl group.

14. An antioxidant of claim 13, wherein $R_8$ is an alkyl group which may optionally have a branched chain.

15. An antioxidant of claim 14, wherein said alkoxycarbonylalkyl group is $-CH_2-COO-n-C10H21$.

16. An antioxidant of claim 5, wherein said alkyl group is a straight or branched alkyl group.

17. An antioxidant of claim 5, wherein the alkyl moiety of said hydroxycarbonylalkyl group is a straight or branched alkyl group.

18. An antioxidant of claim 5, wherein the alkyl moiety of said aralkyl group is a straight or branched alkyl group.